US012714859B2

(12) United States Patent
Gilbert et al.

(10) Patent No.: US 12,714,859 B2
(45) Date of Patent: Aug. 25, 2026

(54) MONITORING CLOSED-LOOP NEURAL STIMULATION THERAPY

(71) Applicant: Saluda Medical Pty Ltd, Level (AU)

(72) Inventors: Samuel Nicholas Gilbert, Artarmon (AU); Daniel John Parker, Artarmon (AU); Dean Michael Karantonis, Artarmon (AU)

(73) Assignee: Saluda Medical Pty Ltd, Macquarie Park (AU)

( * ) Notice: Subject to any disclaimer, the term of this patent is extended or adjusted under 35 U.S.C. 154(b) by 460 days.

(21) Appl. No.: 18/301,117

(22) Filed: Apr. 14, 2023

(65) Prior Publication Data

US 2023/0330418 A1 Oct. 19, 2023

(30) Foreign Application Priority Data

Apr. 15, 2022 (AU) ................................ 2022901021

(51) Int. Cl.
*A61N 1/36* (2006.01)
*A61N 1/372* (2006.01)

(52) U.S. Cl.
CPC ..... *A61N 1/36139* (2013.01); *A61N 1/37247* (2013.01); *A61N 1/3727* (2013.01)

(58) Field of Classification Search
None
See application file for complete search history.

(56) References Cited

U.S. PATENT DOCUMENTS 4,807,643 A 2/1989 Rosier
7,634,315 B2 12/2009 Cholette
8,032,224 B2 10/2011 Miesel et al.
8,579,786 B2 11/2013 Osorio et al.
8,688,221 B2 4/2014 Miesel et al.
9,242,106 B2 1/2016 Klosterman et al.
9,775,530 B2 10/2017 Li et al.
9,888,861 B2 2/2018 Carlson et al.
(Continued)

FOREIGN PATENT DOCUMENTS

WO 2012155183 A1 11/2012
WO 2012155188 A1 11/2012
(Continued)

*Primary Examiner* — Carl H Layno
*Assistant Examiner* — Bryan Mcallister Lee
(74) *Attorney, Agent, or Firm* — Barnes & Thornburg LLP

(57) ABSTRACT

An implantable device for delivering closed-loop neural stimulation therapy. The device comprises: a plurality of electrodes; a stimulus source to provide neural stimuli via the electrodes to a neural pathway; measurement circuitry to process signals sensed at the electrodes; and a control unit. The control unit is configured to: control the stimulus source to provide a first neural stimulus according to a first stimulus parameter; measure an intensity of a neural response evoked by the first stimulus; compute a feedback variable from the neural response; adjust the first stimulus parameter; repeat the control, measure, compute and adjust to maintain the feedback variable at a target response intensity; control the stimulus source to provide, interleaved with the first neural stimuli, a plurality of second neural stimuli according to respective second stimulus parameters; and monitor the therapy by analysing the sensed signals subsequent to each second neural stimulus.

41 Claims, 10 Drawing Sheets

(56) References Cited

U.S. PATENT DOCUMENTS 10,099,057 B2 10/2018 Kent et al.
10,231,650 B2 3/2019 Skelton et al.
10,471,268 B2 11/2019 Crosby et al.
11,076,802 B2 8/2021 Kraiter et al.
11,247,056 B2 2/2022 Hareland et al.
11,247,057 B1 2/2022 Gliner
11,351,376 B2 6/2022 Deshazo et al.
11,471,670 B2 10/2022 Crosby et al.
11,571,566 B2 2/2023 Esteller et al.
11,577,081 B2 2/2023 Crawford
11,583,678 B2 2/2023 Esteller et al.
2009/0306533 A1 12/2009 Rousche et al.
2018/0133507 A1* 5/2018 Malchano ............ A61N 5/0622
2019/0192855 A1 6/2019 Bharmi et al.
2019/0240491 A1 8/2019 Panken et al.
2020/0121912 A1 4/2020 Weiss et al.
2020/0147400 A1 5/2020 Moffitt et al.
2020/0353263 A1 11/2020 Parker et al.
2020/0368532 A1 11/2020 King et al.
2021/0379385 A1 12/2021 Hou et al.
2022/0008726 A1* 1/2022 Corey .................... A61N 1/025
2022/0071513 A1 3/2022 Gunderson
2022/0111213 A1 4/2022 Cassar et al.
2022/0161033 A1 5/2022 Feldman et al.
2022/0193394 A1 6/2022 Feldman et al.
2022/0273953 A1 9/2022 Steinke et al.
2022/0347479 A1 11/2022 Esteller et al.
2022/0387803 A1 12/2022 Zenisek et al.
2023/0067424 A1 3/2023 Crosby et al.
2023/0103448 A1 4/2023 Annoni et al.
2023/0121855 A1 4/2023 Annoni et al.

FOREIGN PATENT DOCUMENTS

WO 2015074121 A1 5/2015
WO 2016090436 A1 6/2016
WO 2020087123 A1 5/2020
WO 2020124135 A1 6/2020
WO 2021007615 A1 1/2021
WO 2022183163 A1 9/2022

* cited by examiner

MONITORING CLOSED-LOOP NEURAL STIMULATION THERAPY

The present application claims priority from Australian Provisional Patent Application No 2022901021 filed on Apr. 15, 2022, the contents of which are incorporated herein by reference in their entirety.

TECHNICAL FIELD

The present invention relates to neural stimulation therapy and in particular to automatic monitoring of, and adaptation of program settings for, neural stimulation therapy out of clinic.

BACKGROUND OF THE INVENTION

There are a range of situations in which it is desirable to apply neural stimuli in order to alter neural function, a process known as neuromodulation. For example, neuromodulation is used to treat a variety of disorders including chronic neuropathic pain, Parkinson's disease, and migraine. A neuromodulation system applies an electrical pulse (stimulus) to neural tissue (fibres, or neurons) in order to generate a therapeutic effect. In general, the electrical stimulus generated by a neuromodulation system evokes a neural response known as an action potential in a neural fibre which then has either an inhibitory or excitatory effect. Inhibitory effects can be used to modulate an undesired process such as the transmission of pain, or excitatory effects may be used to cause a desired effect such as the contraction of a muscle.

When used to relieve neuropathic pain originating in the trunk and limbs, the electrical pulse is applied to the dorsal column (DC) of the spinal cord, a procedure referred to as spinal cord stimulation (SCS). Such a system typically comprises an implanted electrical pulse generator, and a power source such as a battery that may be transcutaneously rechargeable by wireless means, such as inductive transfer. An electrode array is connected to the pulse generator, and is implanted adjacent the target neural fibre(s) in the spinal cord, typically in the dorsal epidural space above the dorsal column. An electrical pulse of sufficient intensity applied to the target neural fibres by a stimulus electrode causes the depolarisation of neurons in the fibres, which in turn generates an action potential in the fibres. Action potentials propagate along the fibres in orthodromic (in afferent fibres this means towards the head, or rostral) and antidromic (in afferent fibres this means towards the cauda, or caudal) directions. Action potentials propagating along Aβ (A-beta) fibres being stimulated in this way inhibit the transmission of pain from a region of the body innervated by the target neural fibres (the dermatome) to the brain. To sustain the pain relief effects, stimuli are applied repeatedly, for example at a frequency in the range of 30 Hz-100 Hz.

For effective and comfortable neuromodulation, it is necessary to maintain stimulus intensity above a recruitment threshold. Stimuli below the recruitment threshold will fail to recruit sufficient neurons to generate action potentials with a therapeutic effect. In almost all neuromodulation applications, response from a single class of fibre is desired, but the stimulus waveforms employed can evoke action potentials in other classes of fibres which cause unwanted side effects. In pain relief, it is therefore desirable to apply stimuli with intensity below a discomfort threshold, above which uncomfortable or painful percepts arise due to over-recruitment of Aβ fibres. When recruitment is too large, Aβ fibres produce uncomfortable sensations. Stimulation at high intensity may even recruit Aδ (A-delta) fibres, which are sensory nerve fibres associated with acute pain, cold and heat sensation. It is therefore desirable to maintain stimulus intensity within a therapeutic range between the recruitment threshold and the discomfort threshold.

The task of maintaining appropriate neural recruitment is made more difficult by electrode migration (change in position over time) and/or postural changes of the implant recipient (patient), either of which can significantly alter the neural recruitment arising from a given stimulus, and therefore the therapeutic range. There is room in the epidural space for the electrode array to move, and such array movement from migration or posture change alters the electrode-to-fibre distance and thus the recruitment efficacy of a given stimulus. Moreover, the spinal cord itself can move within the cerebrospinal fluid (CSF) with respect to the dura. During postural changes, the amount of CSF and/or the distance between the spinal cord and the electrode can change significantly. This effect is so large that postural changes alone can cause a previously comfortable and effective stimulus regime to become either ineffectual or painful.

Another control problem facing neuromodulation systems of all types is achieving neural recruitment at a sufficient level for therapeutic effect, but at minimal expenditure of energy. The power consumption of the stimulation paradigm has a direct effect on battery requirements which in turn affects the device's physical size and lifetime. For rechargeable systems, increased power consumption results in more frequent charging and, given that batteries only permit a limited number of charging cycles, ultimately this reduces the implanted lifetime of the device.

Attempts have been made to address such problems by way of feedback or closed-loop control, such as using the methods set forth in International Patent Publication No. WO2012/155188 by the present applicant. Feedback control seeks to compensate for relative nerve/electrode movement by controlling the intensity of the delivered stimuli so as to maintain a substantially constant neural recruitment. The intensity of a neural response evoked by a stimulus may be used as a feedback variable representative of the amount of neural recruitment. A signal representative of the neural response may be sensed by a measurement electrode in electrical communication with the recruited neural fibres, and processed to obtain the feedback variable. Based on the response intensity, the intensity of the applied stimulus may be adjusted to maintain the response intensity within a therapeutic range.

It is therefore desirable to accurately measure the intensity and other characteristics of a neural response evoked by the stimulus. The action potentials generated by the depolarisation of a large number of fibres by a stimulus sum to form a measurable signal known as an evoked compound action potential (ECAP). Accordingly, an ECAP is the sum of responses from a large number of single fibre action potentials. The ECAP generated from the depolarisation of a group of similar fibres may be measured at a measurement electrode as a positive peak potential, then a negative peak, followed by a second positive peak. This morphology is caused by the region of activation passing the measurement electrode as the action potentials propagate along the individual fibres.

Approaches proposed for obtaining a neural response measurement are described by the present applicant in International Patent Publication No. WO2012/155183, the content of which is incorporated herein by reference.

Closed-loop neural stimulation therapy is governed by a number of parameters to which values must be assigned to implement the therapy. The effectiveness of the therapy depends in large measure on the suitability of the assigned parameter values to the patient undergoing the therapy. As patients vary significantly in their physiological characteristics, a "one-size-fits-all" approach to parameter value assignment is likely to result in ineffective therapy for a large proportion of patients. An important preliminary task, once a neuromodulation device has been implanted in a patient, is therefore to assign values to the therapy parameters that maximise the effectiveness of the therapy the device will deliver to that particular patient. This task is known as programming or fitting the device. Programming generally involves applying certain test stimuli via the device, recording responses, and based on the recorded responses, inferring or calculating the most effective parameter values for the patient. The resulting parameter values are then formed into a "program" that may be loaded to the device to govern subsequent therapy. Some of the recorded responses may be neural responses evoked by the test stimuli, which provide an objective source of information that may be analysed along with subjective responses elicited from the patient. In an effective programming system, the more responses that are analysed, the more effective the eventual assigned parameter values should be.

However, once programming is complete and the patient leaves the clinic, circumstances can change in a way that renders the originally determined program unsuitable. For example, the patient's characteristics may change over time, due to aging or medication regime change. Also, the device characteristics may change over time, due to accretion of scar tissue on the electrode array, or migration of the electrode array within the epidural space. Currently, there is no provision for objective monitoring of neural stimulation therapy to determine whether it remains effective in the face of such changes in circumstances. Rather, patients are expected to request reprogramming if they no longer feel their therapy is effective.

Replicating the initial programming procedures of stimulus and response out of clinic as a method of monitoring neural stimulation therapy may result in discomfort, since the intensity of such stimulation may be above the discomfort threshold for the patient without the benefit of post-operative sedation.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In this specification, a statement that an element may be "at least one of" a list of options is to be understood to mean that the element may be any one of the listed options, or may be any combination of two or more of the listed options.

SUMMARY OF THE INVENTION

Disclosed herein are closed-loop neural stimulation (CLNS) therapy devices and methods configured to provide out of clinic monitoring of CLNS therapy by delivering test stimuli and measuring responses in a way that minimises discomfort and does not disrupt the regular CLNS therapy the patient is receiving. This is achieved by interleaving occasional non-therapeutic ("irregular") stimulus pulses with the regular, therapeutic pulses of the CLNS therapy, and measuring the responses to the irregular stim pulses, without those responses affecting the therapeutic pulses. Rather, the measured responses are used to compute measures of efficacy of the regular therapy without the involvement, or even the knowledge, of the patient. The measures may be compared with respective thresholds or ranges to determine whether the patient needs to be manually reprogrammed. Alternatively, the measures of efficacy may be used to make adjustments to the therapy program without human involvement that counteract any changes in circumstances causing loss of efficacy.

The disclosed technology takes advantage of "psychophysical masking": the hypothesis that single, high intensity stimulus pulses delivered amongst a train of lesser intensity stimulus pulses have a higher discomfort threshold than if delivered in succession. In other words, high intensity stimulus pulses may be delivered above the regular discomfort threshold without causing discomfort, possibly because delivery of a single above-discomfort stimulus pulse would be psychophysically masked by its lower intensity neighbouring pulses.

According to a first aspect of the present technology, there is provided an implantable device for delivering closed-loop neural stimulation therapy. The device comprises: a plurality of electrodes including one or more stimulus electrodes and one or more sense electrodes; a stimulus source configured to provide neural stimuli to be delivered via the one or more stimulus electrodes to a neural pathway of a patient in order to evoke neural responses on the neural pathway; measurement circuitry configured to process signals sensed at the one or more sense electrodes subsequent to each neural stimulus; and a control unit. The control unit is configured to: control the stimulus source to provide a first neural stimulus according to a first stimulus parameter; measure, in the sensed signal, an intensity of a neural response evoked by the first stimulus; compute a feedback variable from the measured intensity of the evoked neural response; and adjust, based on the computed feedback variable, the first stimulus parameter; repeat the controlling, measuring, computing and adjusting to maintain the feedback variable at a target response intensity. The control unit is further configured to: control the stimulus source to provide, interleaved with the first neural stimuli, a plurality of second neural stimuli according to respective second stimulus parameters; and monitor the closed-loop neural stimulation therapy by analysing the sensed signals processed by the measurement circuitry subsequent to each second neural stimulus.

According to a second aspect of the present technology, there is provided an automated method of monitoring closed-loop neural stimulation therapy. The method comprises: delivering a first neural stimulus to a neural pathway of a patient in order to evoke a neural response on the neural pathway, the stimulus being parametrised by a first stimulus parameter; measuring an intensity of the neural response evoked by the first neural stimulus, computing, from the measured intensity, a feedback variable; adjusting, based on the computed feedback variable, the first stimulus parameter; repeating the delivering, measuring, computing and adjusting so as to maintain the feedback variable at a target response intensity; further delivering, interleaved with the first neural stimuli, a plurality of second neural stimuli according to respective second stimulus parameters; receiving a signal sensed subsequent to each delivered second neural stimulus; and monitoring the closed-loop neural stimulation therapy by analysing signals sensed subsequent to each second neural stimulus.

References herein to estimation, determination, comparison and the like are to be understood as referring to an automated process carried out on data by a processor operating to execute a predefined procedure suitable to effect the described estimation, determination and/or comparison step (s). The technology disclosed herein may be implemented in hardware (e.g., using digital signal processors, application specific integrated circuits (ASICs) or field programmable gate arrays (FPGAs)), or in software (e.g., using instructions tangibly stored on non-transitory computer-readable media for causing a data processing system to perform the steps described herein), or in a combination of hardware and software. The disclosed technology can also be embodied as computer-readable code on a computer-readable medium. The computer-readable medium can include any data storage device that can store data which can thereafter be read by a computer system. Examples of the computer-readable medium include read-only memory ("ROM"), random-access memory ("RAM"), magnetic tape, optical data storage devices, flash storage devices, or any other suitable storage devices. The computer-readable medium can also be distributed over network-coupled computer systems so that the computer-readable code is stored and/or executed in a distributed fashion.

BRIEF DESCRIPTION OF THE DRAWINGS

One or more implementations of the invention will now be described with reference to the accompanying drawings, in which.

DETAILED DESCRIPTION OF THE PRESENT TECHNOLOGY

Figure 1:
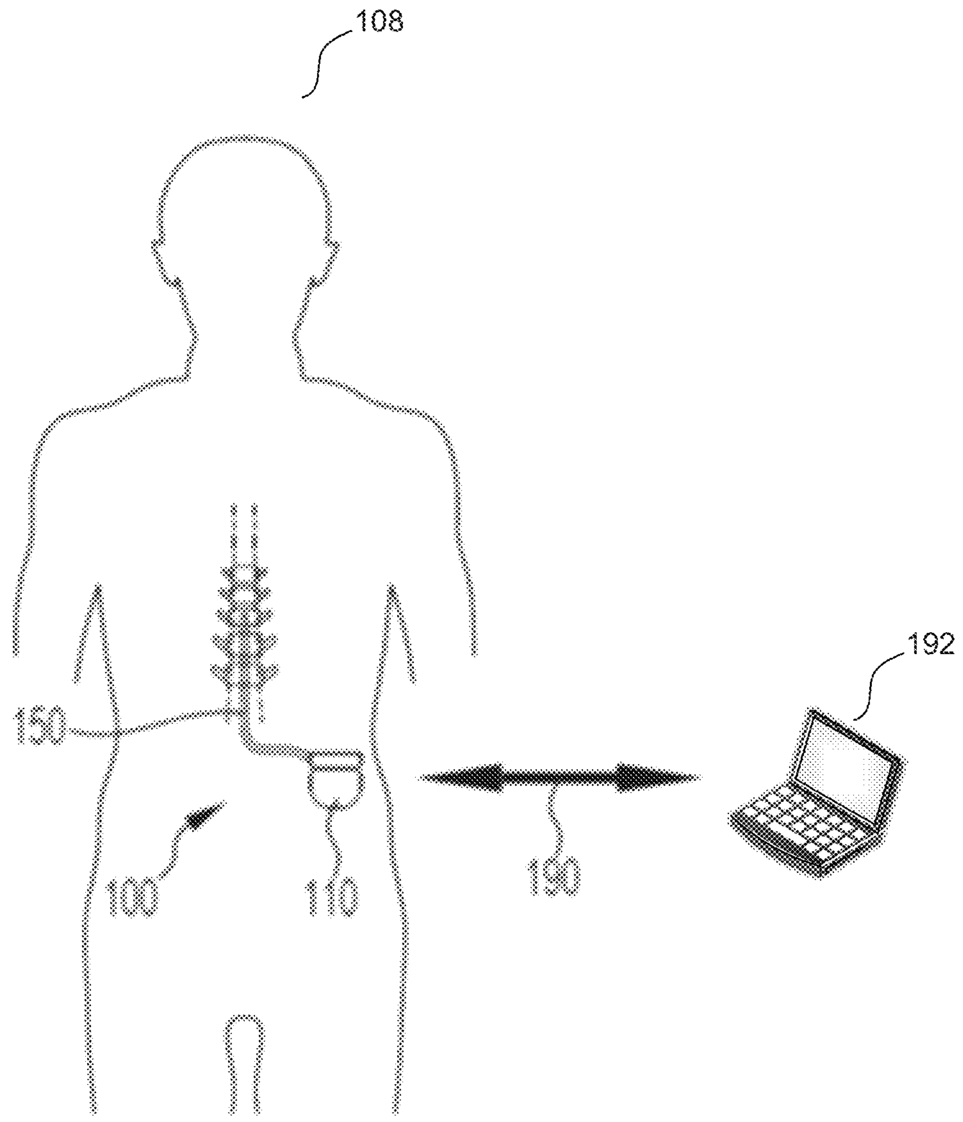
FIG. 1 schematically illustrates an implanted spinal cord stimulator, according to one implementation of the present technology.

FIG. 1 schematically illustrates an implanted spinal cord stimulator 100 in a patient 108, according to one implementation of the present technology. Stimulator 100 comprises an electronics module 110 implanted at a suitable location. In one implementation, stimulator 100 is implanted in the patient's lower abdominal area or posterior superior gluteal region. In other implementations, the electronics module 110 is implanted in other locations, such as in a flank or sub-clavicularly. Stimulator 100 further comprises an electrode array 150 implanted within the epidural space and connected to the module 110 by a suitable lead. The electrode array 150 may comprise one or more electrodes such as electrode pads on a paddle lead, circular (e.g., ring) electrodes surrounding the body of the lead, conformable electrodes, cuff electrodes, segmented electrodes, or any other type of electrodes capable of forming unipolar, bipolar or multipolar electrode configurations for stimulation and measurement. The electrodes may pierce or affix directly to the tissue itself.

Numerous aspects of the operation of implanted stimulator 100 may be programmable by an external computing device 192, which may be operable by a user such as a clinician or the patient 108. Moreover, implanted stimulator 100 serves a data gathering role, with gathered data being communicated to external device 192 via a transcutaneous communications channel 190. Communications channel 190 may be active on a substantially continuous basis, at periodic intervals, at non-periodic intervals, or upon request from the external device 192. External device 192 may thus provide a clinical interface configured to program the implanted stimulator 100 and recover data stored on the implanted stimulator 100. This configuration is achieved by program instructions collectively referred to as the Clinical Programming Application (CPA) and stored in an instruction memory of the clinical interface.

Figure 2:
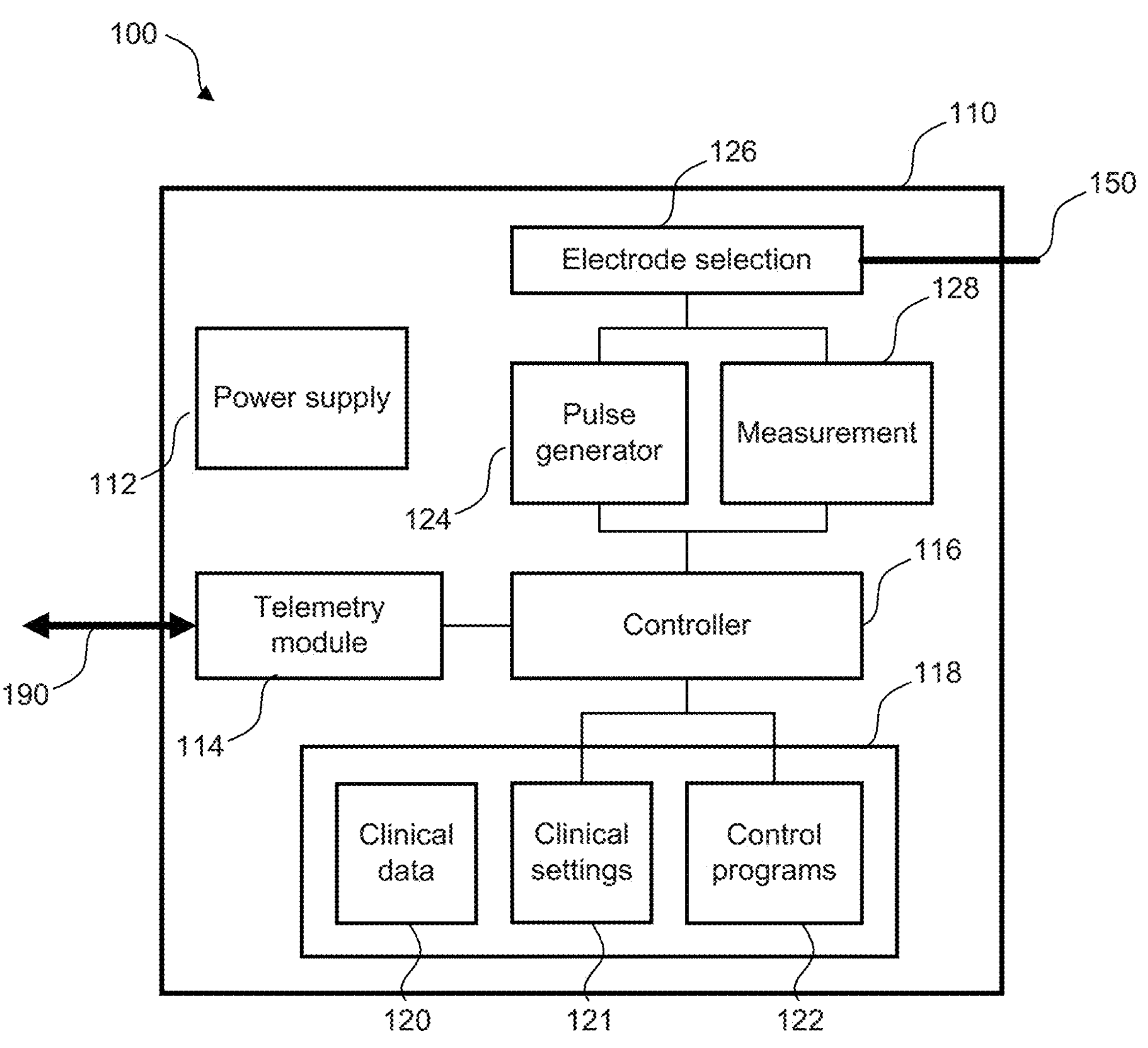
FIG. 2 is a block diagram of the stimulator of FIG. 1.

FIG. 2 is a block diagram of the stimulator 100. Electronics module 110 contains a battery 112 and a telemetry module 114. In implementations of the present technology, any suitable type of transcutaneous communications channel 190, such as infrared (IR), radiofrequency (RF), capacitive and/or inductive transfer, may be used by telemetry module 114 to transfer power and/or data to and from the electronics module 110 via communications channel 190. Module controller 116 has an associated memory 118 storing one or more of clinical data 120, clinical settings 121, control programs 122, and the like. Controller 116 controls a pulse generator 124 to generate stimuli, such as in the form of electrical pulses, in accordance with the clinical settings 121 and control programs 122. Electrode selection module 126 switches the generated pulses to the selected electrode(s) of electrode array 150, for delivery of the pulses to the tissue surrounding the selected electrode(s). Measurement circuitry 128, which may comprise an amplifier and/or an analog-to-digital converter (ADC), is configured to process signals comprising neural responses sensed at measurement electrode(s) of the electrode array 150 as selected by electrode selection module 126.

Figure 3:
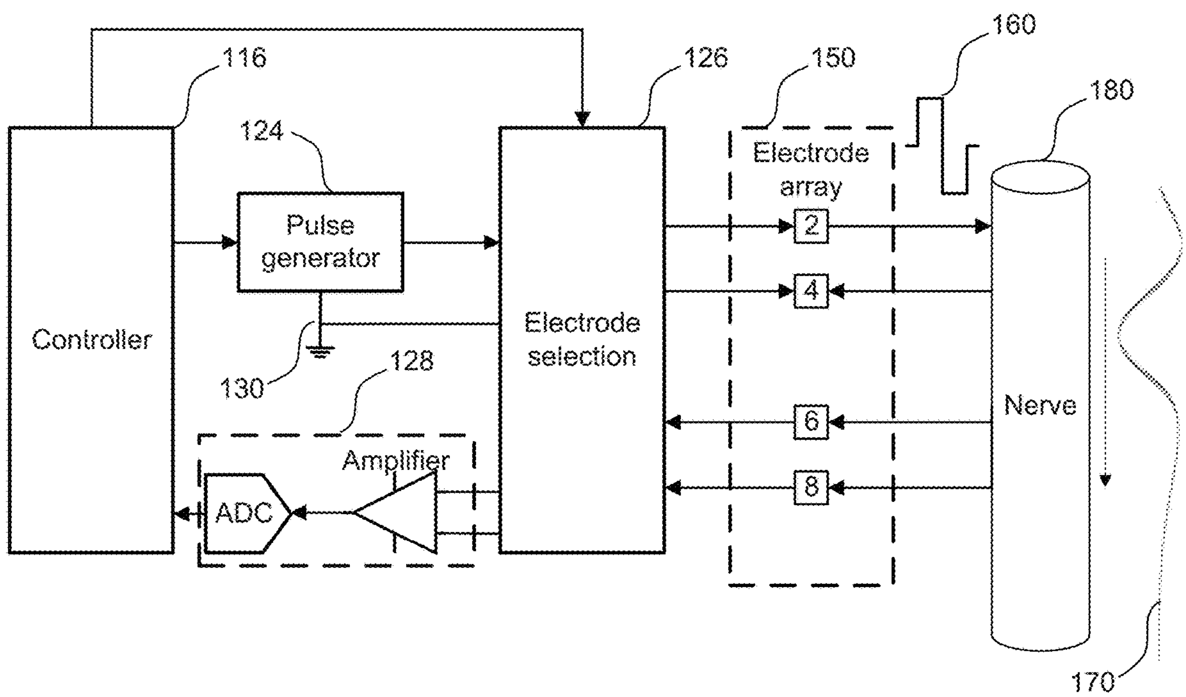
FIG. 3 is a schematic illustrating interaction of the implanted stimulator of FIG. 1 with a nerve.

FIG. 3 is a schematic illustrating interaction of the implanted stimulator 100 with a nerve 180 in the patient 108. In the implementation illustrated in FIG. 3 the nerve 180 may be located in the spinal cord, however in alternative implementations the stimulator 100 may be positioned adjacent any desired neural tissue including a peripheral nerve, visceral nerve, parasympathetic nerve or a brain structure. Electrode selection module 126 selects a stimulus electrode 2 of electrode array 150 through which to deliver a pulse from the pulse generator 124 to surrounding tissue including nerve 180. A pulse may comprise one or more phases, e.g. a biphasic stimulus pulse 160 comprises two phases. Electrode selection module 126 also selects a return electrode 4 of the electrode array 150 for stimulus current return in each phase, to maintain a zero net charge transfer. An electrode may act as both a stimulus electrode and a return electrode over a complete multiphasic stimulus pulse. The use of two electrodes in this manner for delivering and returning current in each stimulus phase is referred to as bipolar stimulation. Alternative embodiments may apply other forms of bipolar stimulation, or may use a greater number of stimulus and/or return electrodes. The set of stimulus and return electrodes and their respective polarities is referred to as the stimulus electrode configuration. Electrode selection module 126 is illustrated as connecting to a ground 130 of the pulse generator 124 to enable stimulus current return via the return electrode 4. However, other connections for current return may be used in other implementations.

Delivery of an appropriate stimulus via stimulus electrodes 2 and 4 to the nerve 180 evokes a neural response 170 comprising an evoked compound action potential (ECAP) which will propagate along the nerve 180 as illustrated at a rate known as the conduction velocity. The ECAP may be evoked for therapeutic purposes, which in the case of a spinal cord stimulator for chronic pain may be to create paraesthesia at a desired location. To this end, the stimulus electrodes 2 and 4 are used to deliver stimuli periodically at any therapeutically suitable frequency, for example 30 Hz, although other frequencies may be used including frequencies as high as the kHz range. In alternative implementations, stimuli may be delivered in a non-periodic manner such as in bursts, or sporadically, as appropriate for the patient 108. To program the stimulator 100 to the patient 108, a clinician may cause the stimulator 100 to deliver stimuli of various configurations which seek to produce a sensation that is experienced by the user as paraesthesia. When a stimulus electrode configuration is found which evokes paraesthesia in a location and of a size which is congruent with the area of the patient's body affected by pain and of a quality that is comfortable for the patient, the clinician or the patient nominates that configuration for ongoing use. The therapy parameters may be loaded into the memory 118 of the stimulator 100 as the clinical settings 121.

Figure 6:
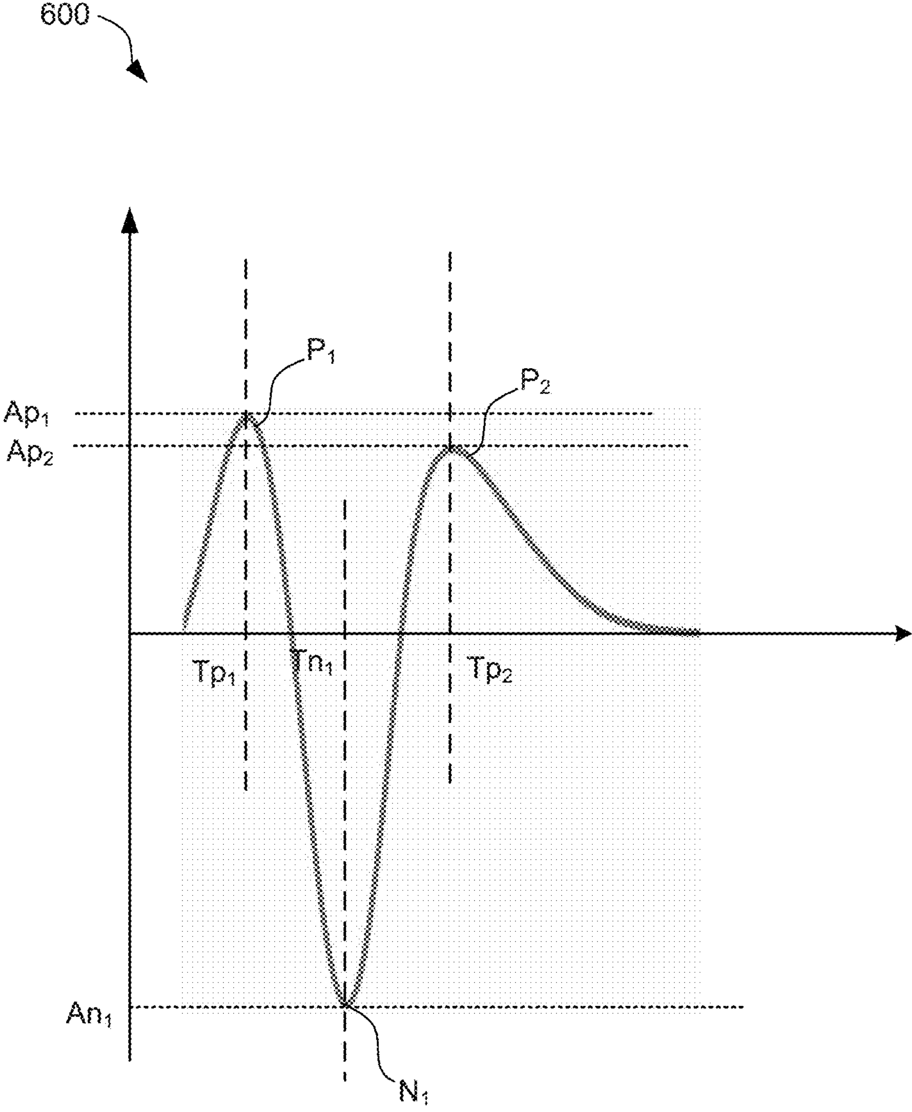
FIG. 6 illustrates the typical form of an electrically evoked compound action potential (ECAP) of a healthy subject.

FIG. 6 illustrates the typical form of an ECAP 600 of a healthy subject, as recorded at a single measurement electrode referenced to the system ground 130. The shape and duration of the single-ended ECAP 600 shown in FIG. 6 is predictable because it is a result of the ion currents produced by the ensemble of fibres depolarising and generating action potentials (APs) in response to stimulation. The evoked action potentials (EAPs) generated synchronously among a large number of fibres sum to form the ECAP 600. The ECAP 600 generated from the synchronous depolarisation of a group of similar fibres comprises a positive peak P1, then a negative peak N1, followed by a second positive peak P2. This shape is caused by the region of activation passing the measurement electrode as the action potentials propagate along the individual fibres.

The ECAP may be recorded differentially using two measurement electrodes, as illustrated in FIG. 3. Differential ECAP measurements are less subject to common-mode noise on the surrounding tissue than single-ended ECAP measurements. Depending on the polarity of recording, a differential ECAP may take an inverse form to that shown in FIG. 6, i.e. a form having two negative peaks N1 and N2, and one positive peak P1. Alternatively, depending on the distance between the two measurement electrodes, a differential ECAP may resemble the time derivative of the ECAP 600, or more generally the difference between the ECAP 600 and a time-delayed copy thereof.

The ECAP 600 may be characterised by any suitable characteristic(s) of which some are indicated in FIG. 6. The amplitude of the positive peak P1 is $Ap_1$ and occurs at time $Tp_1$. The amplitude of the positive peak P2 is $Ap_2$ and occurs at time $Tp_2$. The amplitude of the negative peak P1 is $An_1$ and occurs at time $Tn_1$. The peak-to-peak amplitude is $Ap_1+An_1$. A recorded ECAP will typically have a maximum peak-to-peak amplitude in the range of microvolts and a duration of 2 to 3 ms.

The stimulator 100 is further configured to detect the existence and measure the intensity of ECAPs 170 propagating along nerve 180, whether such ECAPs are evoked by the stimulus from electrodes 2 and 4, or otherwise evoked. To this end, any electrodes of the array 150 may be selected by the electrode selection module 126 to serve as recording electrode 6 and reference electrode 8, whereby the electrode selection module 126 selectively connects the chosen electrodes to the inputs of the measurement circuitry 128. Thus, signals sensed by the measurement electrodes 6 and 8 subsequent to the respective stimuli are passed to the measurement circuitry 128, which may comprise a differential amplifier and an analog-to-digital converter (ADC), as illustrated in FIG. 3. The recording electrode and the reference electrode are referred to as the measurement electrode configuration. The measurement circuitry 128 for example may operate in accordance with the teachings of the above-mentioned International Patent Publication No. WO2012/155183 by the present applicant.

Signals sensed by the measurement electrodes 6, 8 and processed by measurement circuitry 128 are further processed by an ECAP detector implemented within controller 116, configured by control programs 122, to obtain information regarding the effect of the applied stimulus upon the nerve 180. In some implementations, the sensed signals are processed by the ECAP detector in a manner which measures and stores one or more characteristics from each evoked neural response or group of evoked neural responses contained in the sensed signal. In one such implementation, the characteristics comprise a peak-to-peak ECAP amplitude in microvolts (μV). For example, the sensed signals may be processed by the ECAP detector to determine the peak-to-peak ECAP amplitude in accordance with the teachings of International Patent Publication No. WO2015/074121, the contents of which are incorporated herein by reference. Alternative implementations of the ECAP detector may measure and store an alternative characteristic from the neural response, or may measure and store two or more characteristics from the neural response.

Stimulator 100 applies stimuli over a potentially long period such as days, weeks, or months and during this time may store characteristics of neural responses, clinical settings, paraesthesia target level, and other operational parameters in memory 118. To effect suitable SCS therapy, stimulator 100 may deliver tens, hundreds or even thousands of stimuli per second, for many hours each day. Each neural response or group of responses generates one or more characteristics such as a measure of the intensity of the neural response. Stimulator 100 thus may produce such data at a rate of tens or hundreds of Hz, or even kHz, and over the course of hours or days this process results in large amounts of clinical data 120 which may be stored in the memory 118. Memory 118 is however necessarily of limited capacity and care is thus required to select compact data forms for storage into the memory 118, to ensure that the memory 118 is not exhausted before such time that the data is expected to be retrieved wirelessly by external device 192, which may occur only once or twice a day, or less.

Figure 4A:
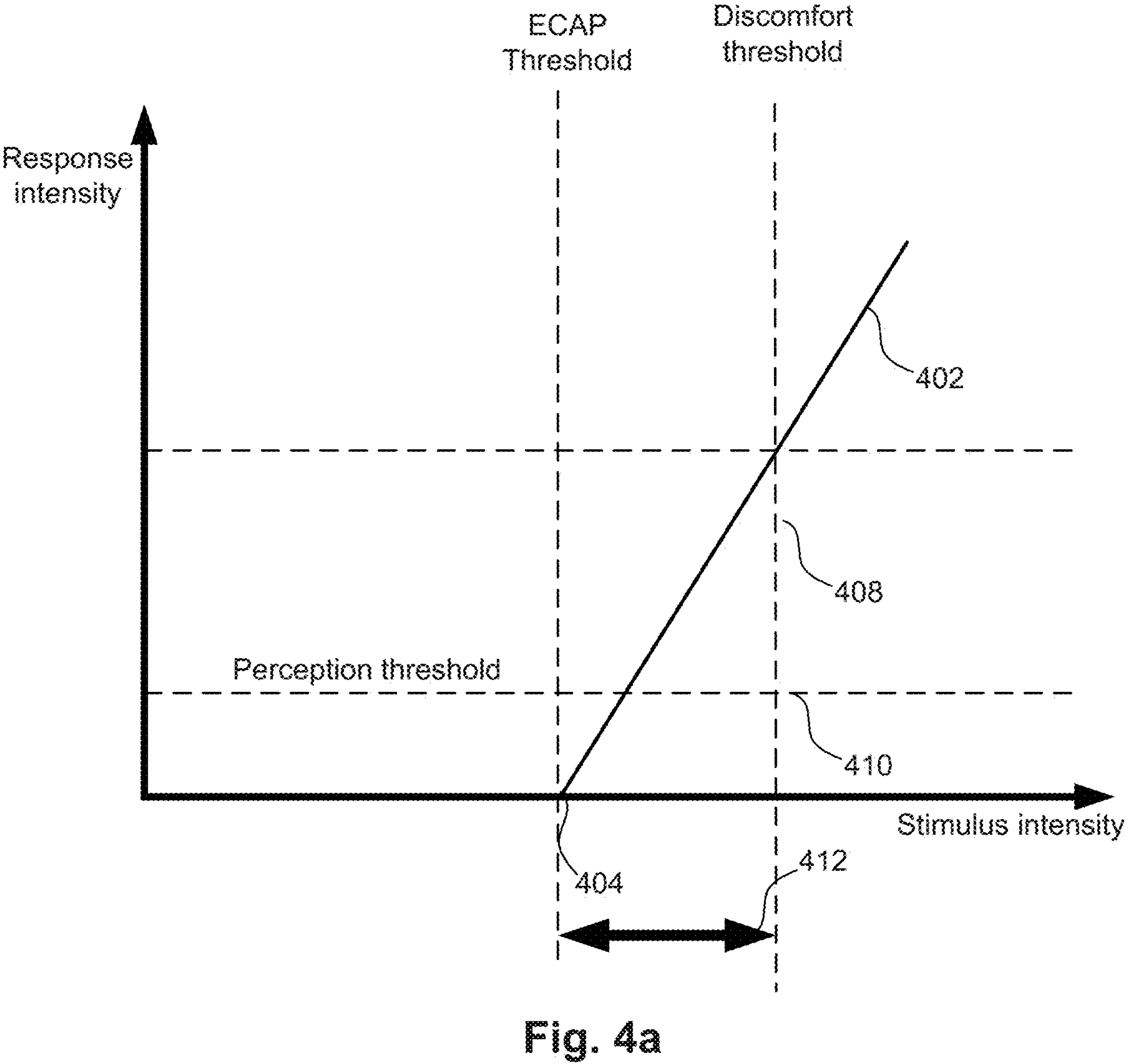
FIG. 4*a* illustrates an idealised activation plot for one posture of a patient undergoing neural stimulation.

An activation plot, or growth curve, is an approximation to the relationship between stimulus intensity (e.g. an amplitude of the current pulse 160) and intensity of neural response 170 resulting from the stimulus (e.g. an ECAP amplitude). FIG. 4*a* illustrates an idealised activation plot 402 for one posture of the patient 108. The activation plot 402 shows a linearly increasing ECAP amplitude for stimulus intensity values above a threshold 404 referred to as the ECAP threshold. The ECAP threshold exists because of the binary nature of fibre recruitment; if the field strength is too low, no fibres will be recruited. However, once the field strength exceeds a threshold, fibres begin to be recruited, and their individual evoked action potentials are independent of the strength of the field. The ECAP threshold 404 therefore reflects the field strength at which significant numbers of fibres begin to be recruited, and the increase in response intensity with stimulus intensity above the ECAP threshold reflects increasing numbers of fibres being recruited. Below the ECAP threshold 404, the ECAP amplitude may be taken to be zero. Above the ECAP threshold 404, the activation plot 402 has a positive, approximately constant slope indicating a linear relationship between stimulus intensity and the ECAP amplitude. Such a relationship may be modelled as:

$$y = \begin{cases} S(s-T), & s \geq T \\ 0, & s < T \end{cases} \quad (1)$$

where s is the stimulus intensity, y is the ECAP amplitude, T is the ECAP threshold and S is the slope of the activation plot (referred to herein as the patient sensitivity). The slope S and the ECAP threshold T are the key parameters of the activation plot 402.

FIG. 4*a* also illustrates a discomfort threshold 408, which is a stimulus intensity above which the patient 108 experiences uncomfortable or painful stimulation. FIG. 4*a* also illustrates a perception threshold 410. The perception threshold 410 corresponds to an ECAP amplitude that is perceivable by the patient. There are a number of factors which can influence the position of the perception threshold 410, including the posture of the patient. Perception threshold 410 may correspond to a stimulus intensity that is greater than the ECAP threshold 404, as illustrated in FIG. 4*a*, if patient 108 does not perceive low levels of neural activation. Conversely, the perception threshold 410 may correspond to a stimulus intensity that is less than the ECAP threshold 404, if the patient has a high perception sensitivity to lower levels of neural activation than can be detected in an ECAP, or if the signal to noise ratio of the ECAP is low.

For effective and comfortable operation of an implantable neuromodulation device such as the stimulator 100, it is desirable to maintain stimulus intensity within a therapeutic range. A stimulus intensity within a therapeutic range 412 is above the ECAP threshold 404 and below the discomfort threshold 408. In principle, it would be straightforward to measure these limits and ensure that stimulus intensity, which may be closely controlled, always falls within the therapeutic range 412. However, the activation plot, and therefore the therapeutic range 412, varies with the posture of the patient 108.

Figure 4B:
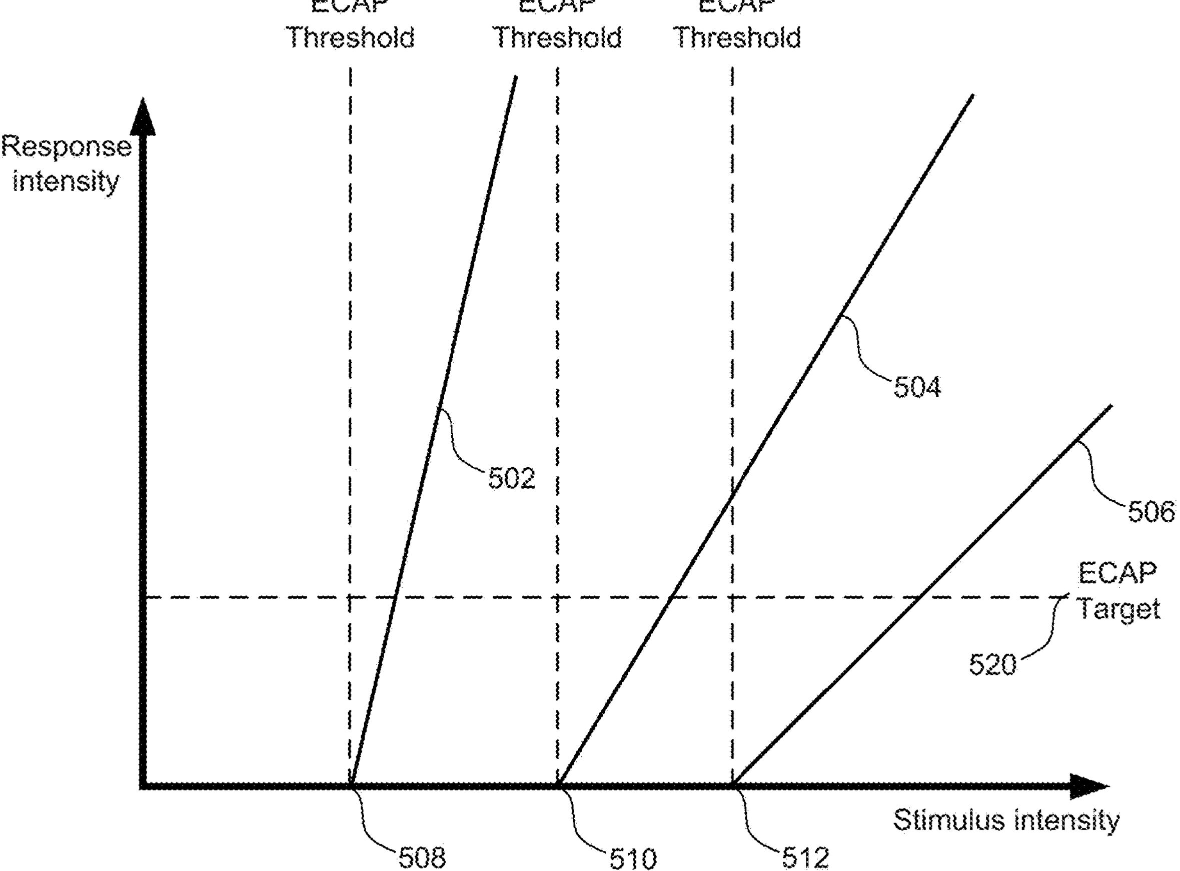
FIG. 4*b* illustrates the variation in the activation plots with changing posture of the patient.

FIG. 4*b* illustrates the variation in the activation plots with changing posture of the patient. A change in posture of the patient may cause a change in impedance of the electrode-tissue interface or a change in the distance between electrodes and the neurons. While the activation plots for only three postures, 502, 504 and 506, are shown in FIG. 4*b*, the activation plot for any given posture can lie between or outside the activation plots shown, on a continuously varying basis depending on posture. Consequently, as the patient's posture changes, the ECAP threshold changes, as indicated by the ECAP thresholds 508, 510, and 512 for the respective activation plots 502, 504, and 506. Additionally, as the patient's posture changes, the slope of the activation plot also changes, as indicated by the varying slopes of activation plots 502, 504, and 506. In general, as the distance between the stimulus electrodes and the spinal cord increases, the ECAP threshold increases and the slope of the activation plot decreases. The activation plots 502, 504, and 506 therefore correspond to increasing distance between stimulus electrodes and spinal cord, and decreasing patient sensitivity.

To keep the applied stimulus intensity within the therapeutic range as patient posture varies, in some implementations an implantable neuromodulation device such as the stimulator 100 may adjust the applied stimulus intensity based on a feedback variable that is determined from one or more measured ECAP characteristics. In one implementation, the device may adjust the stimulus intensity to maintain the measured ECAP amplitude at a target response intensity. For example, the device may calculate an error between a target ECAP amplitude and a measured ECAP amplitude, and adjust the applied stimulus intensity to reduce the error as much as possible, such as by adding the scaled error to the current stimulus intensity. A neuromodulation device that operates by adjusting the applied stimulus intensity based on a measured ECAP characteristic is said to be operating in closed-loop mode and will also be referred to as a closed-loop neural stimulation (CLNS) device. By adjusting the applied stimulus intensity to maintain the measured ECAP amplitude at an appropriate target response intensity, such as a target ECAP amplitude 520 illustrated in FIG. 4*b*, a CLNS device will generally keep the stimulus intensity within the therapeutic range as patient posture varies.

A CLNS device comprises a stimulator that takes a stimulus intensity value and converts it into a neural stimulus comprising a sequence of electrical pulses according to a predefined stimulation pattern. The stimulation pattern is parametrised by multiple parameters including stimulus amplitude, pulse width, number of phases, order of phases, number of stimulus electrode poles (two for bipolar, three for tripolar etc.), and stimulus rate or frequency. At least one of the stimulus parameters, for example the stimulus amplitude, is controlled by the feedback loop.

In an example CLNS system, a user (e.g. the patient or a clinician) sets a target response intensity, and the CLNS device performs proportional-integral-differential (PID) control. In some implementations, the differential contribution is disregarded and the CLNS device uses a first order integrating feedback loop. The stimulator produces stimulus in accordance with a stimulus intensity parameter, which evokes a neural response in the patient. The intensity of an evoked neural response (e.g. an ECAP) is detected, and its amplitude measured by the CLNS device and compared to the target response intensity.

The measured neural response intensity, and its deviation from the target response intensity, is used by the feedback loop to determine possible adjustments to the stimulus intensity parameter to maintain the neural response at the target response intensity. If the target response intensity is properly chosen, the patient receives consistently comfortable and therapeutic stimulation through posture changes and other perturbations to the stimulus/response behaviour.

Figure 5:
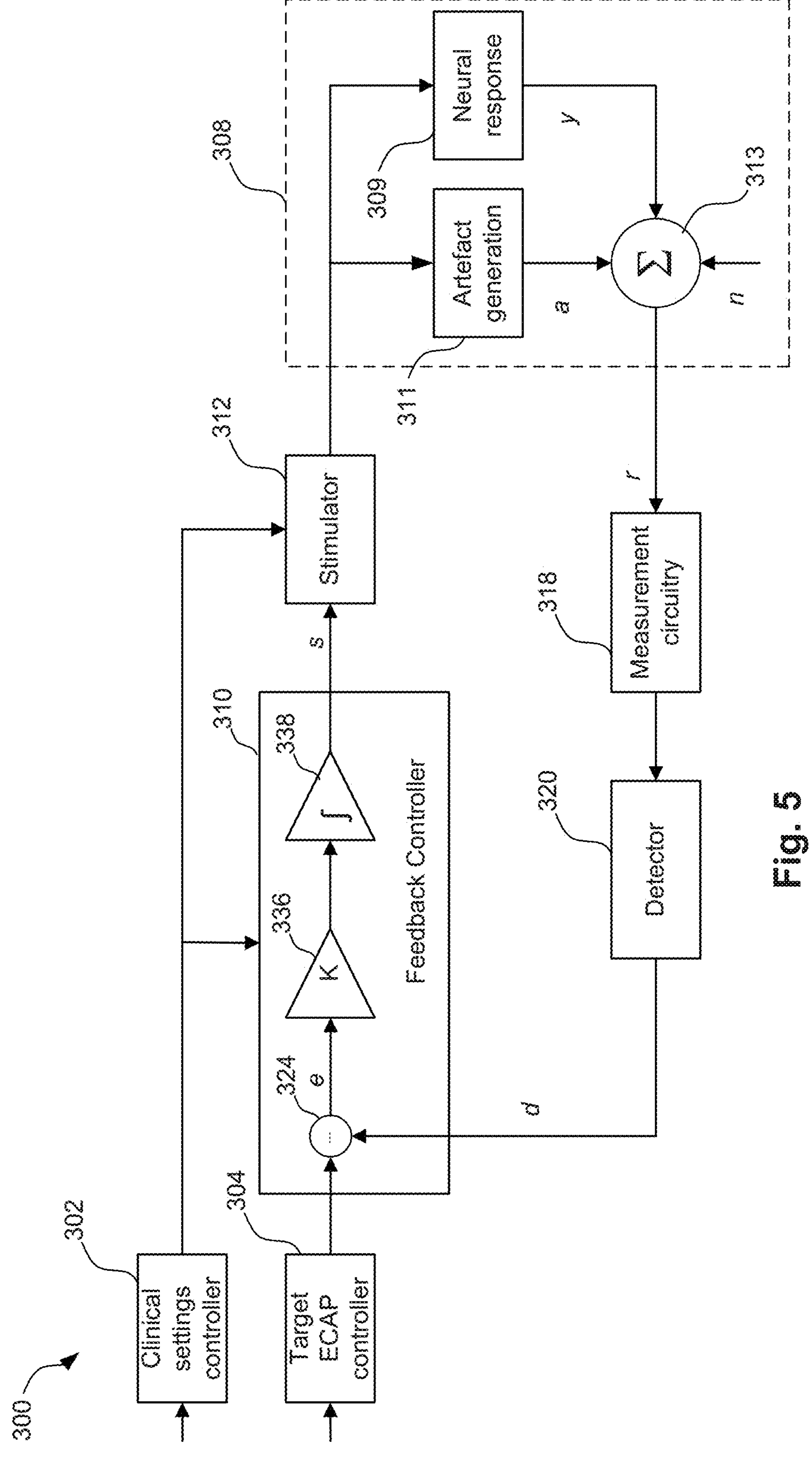
FIG. 5 is a schematic illustrating elements and inputs of a closed-loop neural stimulation system, according to one implementation of the present technology.

FIG. 5 is a schematic illustrating elements and inputs of a closed-loop neural stimulation (CLNS) system 300, according to one implementation of the present technology. The system 300 comprises a stimulator 312 which converts a stimulus intensity parameter (for example a stimulus current amplitude) s, in accordance with a set of predefined stimulus parameters, to a neural stimulus comprising a sequence of electrical pulses on the stimulus electrodes (not shown in FIG. 5). According to one implementation, the predefined stimulus parameters comprise the number and order of phases, the number of stimulus electrode poles, the pulse width, and the stimulus rate or frequency.

The generated stimulus crosses from the electrodes to the spinal cord, which is represented in FIG. 5 by the dashed box 308. The box 309 represents the evocation of a neural response y by the stimulus as described above. The box 311 represents the evocation of an artefact signal a, which is dependent on stimulus intensity and other stimulus parameters, as well as the electrical environment of the measurement electrodes. Various sources of measurement noise n, as well as the artefact a, may add to the evoked response y at the summing element 313 to form the sensed signal r, including electrical noise from external sources such as 50 Hz mains power; electrical disturbances produced by the body such as neural responses evoked not by the device but by other causes such as peripheral sensory input, EEG, EMG, and electrical noise from measurement circuitry 318.

The neural recruitment arising from the stimulus is affected by mechanical changes, including posture changes, walking, breathing, heartbeat and so on. Mechanical changes may cause impedance changes, or changes in the location and orientation of the nerve fibres relative to the electrode array(s). As described above, the intensity of the evoked response provides a measure of the recruitment of the fibres being stimulated. In general, the more intense the stimulus, the more recruitment and the more intense the evoked response. An evoked response typically has a maximum amplitude in the range of microvolts, whereas the voltage resulting from the stimulus applied to evoke the response is typically several volts.

Measurement circuitry 318, which may be identified with measurement circuitry 128, amplifies the sensed signal r (including evoked neural response, artefact, and measurement noise) and samples the amplified sensed signal r to capture a "signal window" comprising a predetermined number of samples of the amplified sensed signal r. The ECAP detector 320 processes the signal window and outputs a measured neural response intensity d. A typical number of samples in a captured signal window is 60. In one implementation, the neural response intensity comprises an ECAP amplitude. The measured response intensity d is input into the feedback controller 310. The feedback controller 310 comprises a comparator 324 that compares the measured response intensity d to a target ECAP amplitude as set by the target ECAP controller 304 and provides an indication of the difference between the measured response intensity d and the target ECAP amplitude. This difference is the error value, e.

The feedback controller 310 calculates an adjusted stimulus intensity parameter, s, with the aim of maintaining a measured response intensity d equal to the target ECAP amplitude. Accordingly, the feedback controller 310 adjusts the stimulus intensity parameters to minimise the error value, e. In one implementation, the controller 310 utilises a first order integrating function, using a gain element 336 and an integrator 338, in order to provide suitable adjustment to the stimulus intensity parameter s. According to such an implementation, the current stimulus intensity parameter s may be computed by the feedback controller 310 as $$s=\int Ke\,dt \quad (2)$$

where K is the gain of the gain element 336 (the controller gain). This relation may also be represented as $$\delta s=Ke$$

where δs is an adjustment to the current stimulus intensity parameter s.

A target ECAP amplitude is input to the comparator 324 via the target ECAP controller 304. In one embodiment, the target ECAP controller 304 provides an indication of a specific target ECAP amplitude. In another embodiment, the target ECAP controller 304 provides an indication to increase or to decrease the present target ECAP amplitude. The target ECAP controller 304 may comprise an input into the neuromodulation device, via which the patient or clinician can input a target ECAP amplitude, or indication thereof. The target ECAP controller 304 may comprise memory in which the target ECAP amplitude is stored, and from which the target ECAP amplitude is provided to the feedback controller 310.

A clinical settings controller 302 provides clinical settings to the system 300, including the gain K for the gain element 336 and the stimulus parameters for the stimulator 312. The clinical settings controller 302 may be configured to adjust the gain K of the gain element 336 to adapt the feedback loop to patient sensitivity. The clinical settings controller 302 may comprise an input into the neuromodulation device, via which the patient or clinician can adjust the clinical settings. The clinical settings controller 302 may comprise memory in which the clinical settings are stored, and are provided to components of the system 300.

In some implementations, two clocks (not shown) are used, being a stimulus clock operating at the stimulus frequency (e.g. 60 Hz) and a sample clock for sampling the sensed signal r (for example, operating at a sampling frequency of 10 kHz). As the ECAP detector 320 is linear, only the stimulus clock affects the dynamics of the CLNS system 300. On the next stimulus clock cycle, the stimulator 312 outputs a stimulus in accordance with the adjusted stimulus intensity s. Accordingly, there is a delay of one stimulus clock cycle before the stimulus intensity is updated in light of the error value e.

Figure 7:
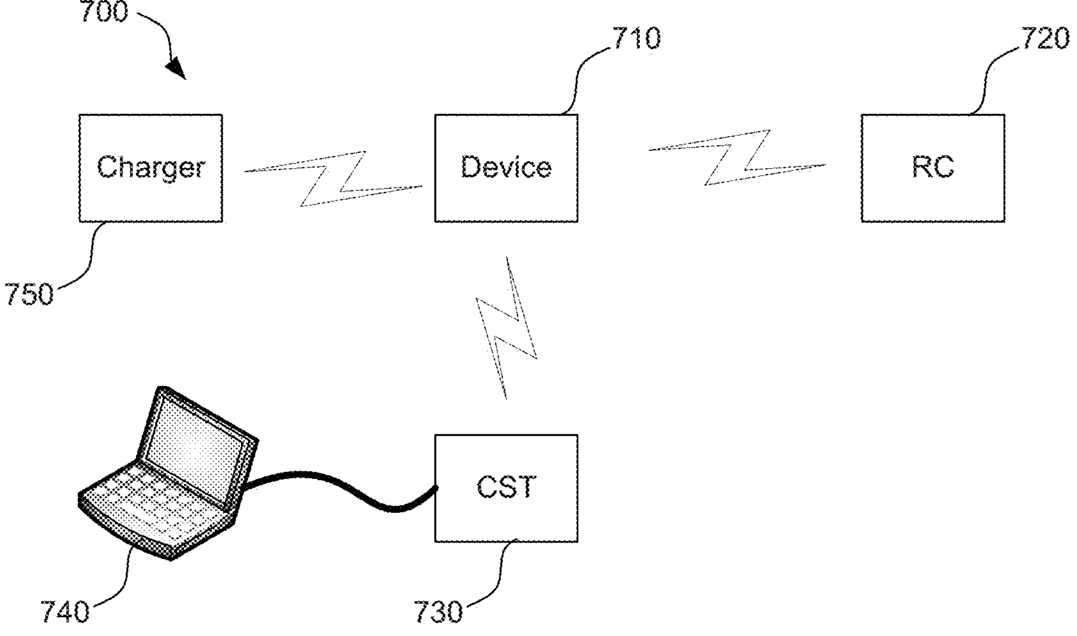
FIG. 7 is a block diagram of a neural stimulation therapy system including the implanted stimulator of FIG. 1 according to one implementation of the present technology.

FIG. 7 is a block diagram of a neural stimulation system 700. The neural stimulation system 700 is centred on a neuromodulation device 710. In one example, the neuromodulation device 710 may be implemented as the stimulator 100 of FIG. 1, implanted within a patient (not shown). The neuromodulation device 710 is connected wirelessly to a remote controller (RC) 720. The remote controller 720 is a portable computing device that provides the patient with control of their stimulation in the home environment by allowing control of the functionality of the neuromodulation device 710, including one or more of the following functions: enabling or disabling stimulation; adjustment of stimulus intensity or target neural response intensity; and selection of a stimulation control program from the control programs stored on the neuromodulation device 710.

The charger 750 is configured to recharge a rechargeable power source of the neuromodulation device 710. The recharging is illustrated as wireless in FIG. 7 but may be wired in alternative implementations.

The neuromodulation device 710 is wirelessly connected to a Clinical System Transceiver (CST) 730. The wireless connection may be implemented as the transcutaneous communications channel 190 of FIG. 1. The CST 730 acts as an intermediary between the neuromodulation device 710 and the Clinical Interface (CI) 740, to which the CST 730 is connected. A wired connection is shown in FIG. 7, but in other implementations, the connection between the CST 730 and the CI 740 is wireless.

The CI 740 may be implemented as the external computing device 192 of FIG. 1. The CI 740 is configured to program the neuromodulation device 710 and recover data stored on the neuromodulation device 710. This configuration is achieved by program instructions collectively referred to as the Clinical Programming Application (CPA) and stored in an instruction memory of the CI 740.

Therapy Monitoring

According to aspects of the present technology, a CLNS system may be monitored out of clinic by delivering stimulus pulses and measuring characteristics of the neural responses evoked by the stimulus pulses. The stimulus pulses used for such monitoring need not be the regular stimulus pulses delivered as part of the CLNS therapy. Instead, according to the present technology, the stimulus pulses delivered for monitoring purposes may be delivered interleaved with, by being mixed by alternating with, the regular, therapeutic stimulus pulses, that is, the stimulus pulses are mixed by alternating with the regular, therapeutic stimulus pulses. The stimulus pulses are also delivered at lower frequency than the regular pulses. Such “irregular” pulses may be of sufficient intensity to evoke neural responses such as ECAPs. However, the measurements of neural responses evoked by the irregular stimulus pulses are not used to adjust the intensity of the therapeutic stimulus pulses. The intensity of the irregular stimulus pulses may even on occasion be above the discomfort threshold. However, isolated high intensity stimulus pulses delivered interleaved with a train of lesser intensity regular stimulus pulses have a higher discomfort threshold than if delivered in succession. In other words, high intensity irregular stimulus pulses may be delivered above the regular discomfort threshold without causing discomfort because delivery of an isolated above-discomfort stimulus pulse may be psychophysically masked by its lower intensity neighbouring pulses.

Figure 8:
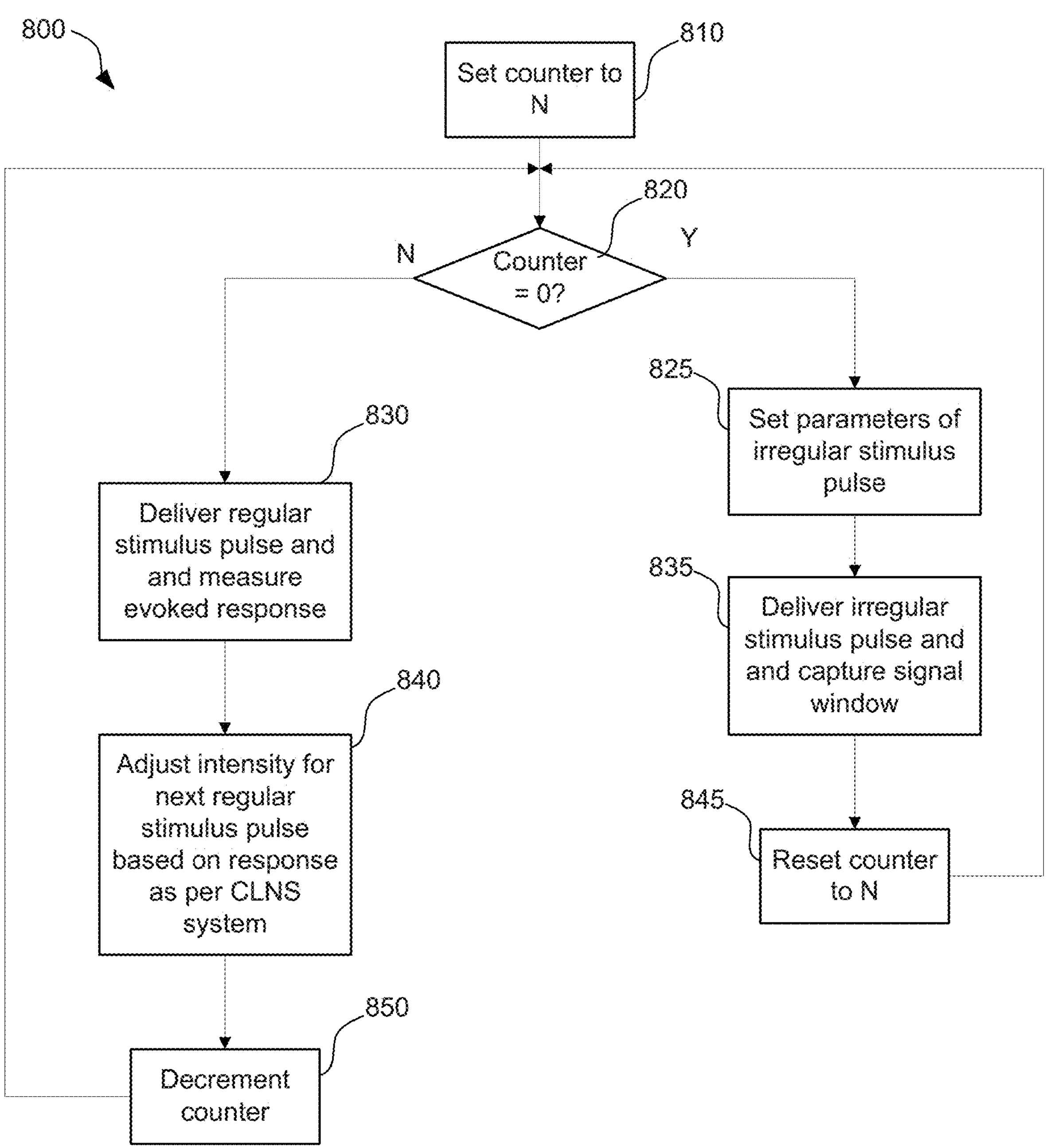
FIG. 8 is a flowchart illustrating a method of interleaving irregular stimulus pulses with regular therapy pulses according to one implementation of the present technology.

In one implementation of the interleaving of irregular pulses for monitoring purposes, the irregular pulses replace one in every N regular CLNS therapy pulses, where N is a large integer such as 50. FIG. 8 is a flowchart illustrating a method 800 of interleaving irregular stimulus pulses with regular CLNS therapy pulses as part of a therapy monitoring process according to one implementation of the present technology. The method 800 may be carried out by the controller, e.g. the controller 116, of the CLNS device 710.

The method 800 starts at step 810, which sets a counter to N. In one implementation, N is 50, such that for a stimulus frequency of 50 Hz, one irregular pulse is delivered every second. Step 820 then checks whether the counter value is zero. If not (“N”), step 830 delivers a regular therapy pulse using the current stimulus electrode configuration (SEC), and measures the evoked response as described above using the current measurement electrode configuration (MEC). Step 840 then adjusts the intensity for the next regular therapy pulse based on the measured evoked response as described above in relation to the CLNS system 300. Step 850 then decrements the counter, and control returns to step 820.

If the counter value has reached zero (“Y”), step 825 sets the parameters of the next irregular stimulus pulse. The setting of parameters such as pulse width, intensity, number of phases, and phase order in step 825 depends on the nature of the monitoring being carried out via the irregular stimulus pulses. Various implementations of monitoring via irregular stimulus pulses are described below. Step 835 then delivers the irregular stimulus pulse, possibly via the same SEC as used in step 830, using the parameters set in step 825, and captures the resulting signal window using an MEC that depends on the nature of the monitoring being carried out via the irregular stimulus pulses. Step 835 may also involve some further processing of the sensed signal depending on the nature of the monitoring being carried out via the irregular stimulus pulses. Step 845 then resets the counter to N, and processing returns to step 820.

In one aspect of the present technology, the irregular pulses are delivered and the corresponding signal windows are captured in step 835 using the current MEC as used in step 830. The quality of the evoked neural responses in the captured signal windows is assessed. The resulting quality assessments, quantified as a quality measure, may be used to determine whether the current MEC remains suitable for the current circumstances. Suitability may be determined by comparing the quality measure to a threshold. If the quality measure falls below the threshold, the monitoring process may provide an indication to the patient, such as via a user interface on their remote controller 720, that the current MEC is no longer suitable. In some implementations, the monitoring process may also assess the quality of the evoked neural responses obtained using alternative MECs. The resulting quality assessments may be used to recommend, or automatically switch to, an alternative MEC. In one such implementation, the alternative MEC is the one with the highest quality measure of evoked neural responses.

International Patent Publication no. WO2021/007615, by the present applicant, the contents of which are herein incorporated by reference, discloses one method of obtaining a quality measure, namely a Signal Quality Indicator (SQI), from a collection of measurements of intensities of evoked responses to delivered stimuli of intensities spanning the therapeutic range and having a constant pulse width. The evoked response intensities may be measured by an ECAP detector such as the ECAP detector 320 described above. In one implementation, the correlation-based ECAP detector described in the above-mentioned International Patent Publication no. WO2015/074121 may be used. The correlation-based ECAP detector is insensitive to the presence of artefact in the sensed signal. The SQI is a decimal number from 0 to 1 that characterises a set of recordings, loosely defined as the quality of the growth curve that would be measured from the recordings.

In an alternative implementation of the quality assessment aspect, a process called the Activation Plot builder (AP Builder) may be used to compute a quality measure referred to as the Growth Curve Quality Indicator (GCQI) from a set of measurements of intensities of evoked responses to delivered stimuli of various intensities. The AP builder fits a model referred to as the Logistic Growth Curve (LGC) to a set of (s, d) value pairs, where d is a measured ECAP amplitude from a captured signal window and s is the corresponding stimulus intensity.

In one implementation, the LGC model is a four-parameter function:

$$d(s) = A + \frac{K - A}{1 + \exp(-B(s - M))} \tag{3}$$

where the four parameters are:

A, the minimum value (the detected ECAP amplitude in the absence of stimulation)

K, the maximum value (the detected ECAP amplitude at which saturation occurs, i.e. increases in stimulus intensity do no increase the detected ECAP amplitude)

M, the current amplitude at the midpoint between A and K

B, the steepness of the LGC, which is proportional to the gradient at the midpoint between A and K.

In other implementations, fewer parameters may be used for the LGC model, for example an LGC model in which the minimum value A is identically zero. In yet other implementations, other parametrised functions may be fit by the AP builder to the set of (s, d) value pairs.

To fit the LGC, the parameters A, K, M, and B may be initialised to sensible starting points $A_0$, $K_0$, $M_0$, and $B_0$. In one implementation, these values may be set to:

$A_0$: the mean of the ECAP amplitudes obtained from the lowest few stimulus current amplitudes.

$K_0$: the mean of the ECAP amplitudes obtained from the highest few stimulus current amplitudes.

$M_0$: the stimulus current amplitude at the midpoint between A and K $B_0$: may be calculated from the gradient m at the midpoint, obtained from local linear regression of value pairs acquired near the midpoint, as $B_0=m*4/(K_0-A_0)$.

An optimisation algorithm such as Trust Region Reflective (TRF) may then be used to optimise the four parameters A, K, M, and B from their starting points $A_0$, $K_0$, $M_0$, and $B_0$.

Figure 9:
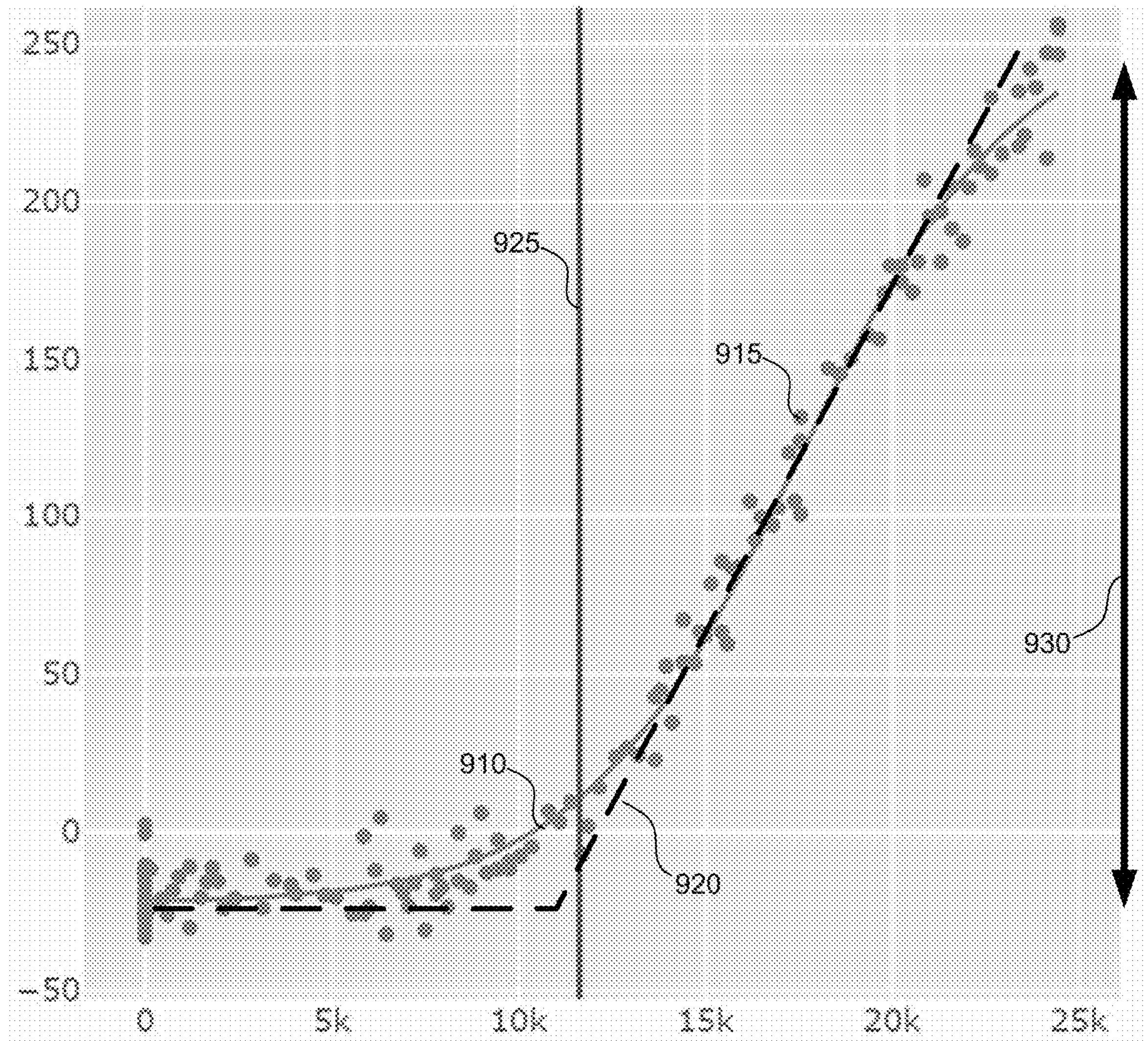
FIG. 9 shows a fitted LGC model to a set of (stimulus intensity, response intensity) value pairs, alongside a piecewise linear model fit to the same data.

FIG. 9 shows a fitted LGC model 910 to a set of (s, d) value pairs, e.g. the pair 915, alongside a piecewise linear model 920 fit to the same data. The superior fit of the LGC model to the data at both low and high stimulus current amplitudes is evident. The ECAP threshold 925 as estimated from the fitted LGC as described below is also illustrated.

The AP builder then calculates a growth curve quality index (GCQI) for the fitted LGC model. The GCQI indicates a signal-to-noise ratio (SNR) of the fitted LGC. In one implementation, the AP builder may calculate the GCQI by dividing the peak-to-peak amplitude of the fitted LGC (e.g. as indicated in FIG. 9 by the arrow 930) by the standard deviation of the residuals of the fitted LGC.

According to another aspect of the present technology, the irregular pulses are delivered with various stimulus parameters, and key parameters of the patient's response to stimulation are estimated from measurements of the evoked neural responses in the captured signal windows. In some implementations, an activation plot model such as a piecewise linear model 920 or an LGC 910 is fitted to the measurements of evoked neural responses obtained at various stimulus intensities using the current MEC. The key parameters of the patient's response to stimulation, such as the ECAP threshold $I_{thresh}$ and the patient sensitivity S, are obtained from the fitted activation plot.

In one implementation of the key parameter estimation aspect, a fitted LGC such as the LGC 910 may be used to estimate the ECAP threshold $I_{thresh}$. In this implementation, a line may be constructed through the midpoint M of the fitted LGC with slope B. The ECAP threshold $I_{thresh}$ may be estimated as the stimulus current amplitude s at which the constructed line intersects the minimum value A. It may be shown that the resulting ECAP threshold $I_{thresh}$ is given by $$I_{thresh} = M - \frac{2}{B} \tag{4}$$

The fitted LGC may also be used to estimate the patient sensitivity S. In this implementation, the patient sensitivity S is the slope of the fitted LGC at its midpoint M, which may be computed from the steepness B as follows:

$$S = \frac{B}{4}(K - A) \tag{5}$$

In another implementation of the key parameter estimation aspect, a fitted piecewise linear model such as the model 920 may be used to estimate the ECAP threshold $I_{thresh}$. In such an implementation, the ECAP threshold $I_{thresh}$ is the intercept of the upwardly-sloping portion of the piecewise linear model 920 with the s-axis. The fitted piecewise linear model such as the model 920 may also be used to estimate the patient sensitivity S. In such an implementation, the patient sensitivity S is the slope of the upwardly-sloping portion of the piecewise linear model.

Other key parameters of the patient's response to stimulation that may be estimated from the measurements of evoked responses according to the key parameter estimation aspect include chronaxie, rheobase, and conduction velocity. The threshold for action potential generation in a neuron follows a strength-duration curve. As the pulse width of the stimulus is increased, the intensity of stimulus needed to activate a neuron decreases. The rheobase is an asymptotic value, being the largest stimulus intensity that is incapable of evoking an action potential in the target tissue even at very long pulse widths. The chronaxie is defined as the minimum pulse width required to evoke an action potential at a current that is twice the rheobase. Measurement of the strength-duration curve by estimating the ECAP threshold at a range of pulse widths allows determination of the chronaxie and rheobase.

The conduction velocity is the speed at which the ECAP propagates along the dorsal column. The conduction velocity may be measured by measuring the latency of an ECAP, that is, the time delay between the irregular stimulus pulse that evokes the ECAP and the time of arrival of the ECAP at the recording electrode. The time of arrival may be estimated from the time within the captured signal window of a prominent feature of the ECAP such as the P2 peak. The distance between the stimulus electrode and the recording electrode divided by the latency gives the conduction velocity. This distance may be known accurately if the SEC and the MEC are located on the same electrode array. Other implementations of measuring the conduction velocity, including those using measured evoked responses from multiple MECs, are described in International Patent Publication no. WO2020/087123, by the present applicant, the contents of which are herein incorporated by reference.

Another key parameter of the patient's response to stimulation that may be estimated from the evoked responses according to the key parameter estimation aspect is the "late" or "slow" evoked response threshold. Slow responses are described in International Patent Publication no. WO2012/155188 by the present applicant. In one such implementation, the irregular pulses are delivered with high intensity, and the late response threshold is measured from the late responses identifiable in the evoked responses. In one implementation, the late response is measured as the lowest stimulus intensity at which a late response is consistently detectable as part of the evoked response.

If any of the key parameters of the patient's response to stimulation estimated according to the key parameter estimation aspect departs from a reasonable range, an indication may be communicated to the patient, for example through their remote controller 720, that a reprogramming visit may be required. In another such implementation, suitable when the key parameter is the late response threshold, if the intensity of the regular stimulus pulses is consistently close to the late response threshold, an indication may be provided to the patient, for example through their remote controller 720, that a reprogramming visit may be required.

In some implementations of the key parameter estimation aspect, one or more of the key parameters may be used to adjust the clinical settings 121 of the CLNS therapy stored within the memory 118 of the CLNS device 710. In one such implementation, the gain K of the gain element 336 may be set using the patient sensitivity S. International Patent Publication no. WO2016/090436, by the present applicant, the contents of which are herein incorporated by reference, discloses a method of setting the controller gain K inversely proportionally to the patient sensitivity S. The constant of inverse proportionality is related to the corner frequency of the low-pass filter formed by the closed-loop system 300 of FIG. 5. As disclosed in International Patent Publication no. WO2016/090436, the corner frequency is set as a compromise between attenuation of electrical noise and attenuation of periodic anatomical perturbations to the patient sensitivity, such as heartbeat.

According to another aspect of the present technology, the irregular pulses are delivered and the measured evoked responses in the captured signal windows are used to estimate the position of the electrode array relative to the patient's anatomy, or if there are multiple electrode arrays, their position relative to each other. In one implementation of the array position estimation aspect, the latency of the evoked responses measured using an MEC on the opposite array to the array on which the current SEC is located may be used to estimate the longitudinal or rostro-caudal position of the MEC array relative to the SEC array. In one such implementation, Lead 1 and Lead 2 have 12 contacts, 3 mm in length with 4 mm spacing (i.e. pitch of 7 mm). The respective ECAP N1 peak latencies at E6, E7 (sixth and seventh contacts on Lead 1), and E4 (4th contact on Lead 2) respectively, namely t_E6, t_E7, and t_E4, may be measured. The ECAP latency on E4 falls between the ECAP latency of E6 and E7. It is known that Distance (d)=Speed (s)*Time (t). The distance d_lead1 between E6 and E7 is known to be 7 mm. The conduction velocity of the ECAP may be estimated as $$s\_\text{lead1}=d\_\text{lead1}/(t\_E7-t\_E6)$$

and then the distance d between E6 (Lead 1) and E4 (Lead 2) (the position of Lead 2 relative to Lead 1) may be estimated as $$d=s\_\text{lead1}*(t\_E4-t\_E6)$$

In another implementation of the array position estimation aspect, late responses are related to the activation of dorsal roots, and therefore the threshold of late responses can be used to estimate identify the medio-lateral location of the array. For example, if two electrode arrays are implanted and the late response threshold is lower on one array, this would indicate that that array is closer to the dorsal roots than the other array.

If the relative array position estimated according to the array position estimation aspect departs from a reasonable range, an indication may be communicated to the patient, for example through their remote controller 720, that a reprogramming visit may be required.

In some implementations of the array position estimation aspect, the array position estimate may be used to adjust the clinical settings 121 of the CLNS therapy stored within the memory 118 of the CLNS device 710. In one such implementation, if the rostro-caudal position of the array on which the current MEC is located has changed relative to the rostro-caudal position of the array on which the SEC is located since implantation and programming, the current MEC may be changed by an equal and opposite amount, so that it regains its original position relative to the SEC.

According to another aspect of the present technology, the irregular pulses are delivered and the captured signal windows are analysed to estimate the amount of artefact present in the signal windows. International Patent Publication no. WO2020/124135 by the present applicant, the contents of which are herein incorporated by reference, describes how the artefact component in a captured signal window may be estimated using a model-based approach. In implementations of the artefact estimation aspect, the intensity of the irregular stimulus pulses may be set below the ECAP threshold to ensure they evoke few or no neural responses. This eases the task of estimating the artefact component in the captured signal windows using the model-based approach. An amount of artefact may then be estimated from the artefact components in the signal windows. Alternatively, a representative artefact signal may be obtained from the artefact components in the signal windows, e.g. by averaging the artefact components.

If the amount of artefact estimated from the artefact components departs from a reasonable range, an indication may be communicated to the patient, for example through their remote controller 720, that a reprogramming visit may be required.

In some implementations of the artefact estimation aspect, the representative artefact signal may be used to adjust the clinical settings 121 of the CLNS therapy stored within the memory 118 of the CLNS device 710. In one such implementation, the parameters of the ECAP detector 320 may be adjusted based on the representative artefact signal to improve the insensitivity to artefact of the ECAP detector. In one such implementation in which the correlation-based ECAP detector described in the above-mentioned International Patent Publication no. WO2015/074121 is used, the representative artefact signal may be used to adjust the coefficients of the correlation template to improve the insensitivity to artefact of the correlation-based ECAP detector.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not limiting or restrictive.

LABEL LIST

| | |
|---|---|
| stimulator | 100 |
| patient | 108 |
| electronics module | 110 |
| battery | 112 |
| telemetry module | 114 |
| controller | 116 |
| memory | 118 |
| clinical data | 120 |
| clinical settings | 121 |
| control programs | 122 |
| pulse generator | 124 |
| electrode selection module | 126 |
| measurement circuitry | 128 |
| ground | 130 |
| electrode array | 150 |
| stimulus pulse | 160 |
| neural response | 170 |
| nerve | 180 |
| transcutaneous communications channel | 190 |
| external computing device | 192 |
| closed - loop neural stimulation system | 300 |
| clinical settings controller | 302 |
| target ECAP controller | 304 |
| box | 308 |
| box | 309 |
| feedback controller | 310 |
| box | 311 |
| stimulator | 312 |
| element | 313 |
| measurement circuitry | 318 |
| ECAP detector | 320 |
| comparator | 324 |
| gain element | 336 |
| integrator | 338 |
| activation plot | 402 |
| ECAP threshold | 404 |
| discomfort threshold | 408 |
| perception threshold | 410 |
| therapeutic range | 412 |
| activation plot | 502 |
| activation plot | 504 |
| activation plot | 506 |
| ECAP threshold | 508 |
| ECAP threshold | 510 |
| ECAP threshold | 512 |
| ECAP target | 520 |
| single - ended ECAP | 600 |
| neural stimulation system | 700 |
| neuromodulation device | 710 |
| remote controller | 720 |
| clinical system transceiver | 730 |
| clinical interface | 740 |
| charger | 750 |
| method | 800 |
| step | 810 |
| step | 820 |
| step | 825 |
| step | 830 |
| step | 835 |
| step | 840 |
| step | 845 |
| step | 850 |
| logistic growth curve model | 910 |
| pair | 915 |
| linear model | 920 |
| threshold | 925 |
| arrow | 930 |

The invention claimed is:

1. An implantable device for delivering closed-loop neural stimulation therapy, the device comprising:

a plurality of electrodes including one or more stimulus electrodes and one or more sense electrodes;

a stimulus source configured to provide neural stimuli to be delivered via the one or more stimulus electrodes to a neural pathway of a patient in order to evoke neural responses on the neural pathway;

measurement circuitry configured to capture signals sensed at the one or more sense electrodes subsequent to each neural stimulus; and a control unit configured to deliver closed-loop neural stimulation therapy by:

controlling the stimulus source to provide a first neural stimulus according to a first stimulus parameter;

measuring, in the sensed signal, an intensity of a neural response evoked by the first neural stimulus;

computing a feedback variable from the measured intensity of the evoked neural response;

adjusting, based on the computed feedback variable, the first stimulus parameter; and repeating the controlling, measuring, computing and adjusting to maintain the feedback variable at a target response intensity, wherein the control unit is further configured to:

control the stimulus source to provide, interleaved with the first neural stimuli, a plurality of second neural stimuli according to respective second stimulus parameters, wherein the second neural stimuli are different from the first neural stimuli; and monitor the closed-loop neural stimulation therapy by analysing the sensed signals captured by the measurement circuitry subsequent to respective second neural stimuli of the plurality of second neural stimuli.

2. The device of claim 1, wherein the control unit is configured to monitor the therapy by:

measuring, in each sensed signal, an intensity of a neural response evoked by the corresponding second neural stimulus.

3. The device of claim 2, wherein the control unit is further configured to measure a quality of the evoked neural responses from the measured intensities of the evoked neural responses.

4. The device of claim 3, wherein the control unit is further configured to:

compare the measured quality with a threshold; and communicate, based on the comparison, an indicator to the patient.

5. The device of claim 3, wherein the control unit is further configured to:

adjust a clinical setting of the closed-loop neural stimulation therapy based on the measured quality.

6. The device of claim 2, wherein the control unit is further configured to estimate one or more key parameters of the response of the neural pathway to stimuli from the measured intensities of the neural responses.

7. The device of claim 6, wherein the control unit is configured to estimate the one or more key parameters by fitting an activation plot to the measured intensities of the neural responses.

8. The device of claim 7, wherein the activation plot is a Logistic Growth Curve (LGC).

9. The device of claim 7, wherein the one or more key parameters comprises a sensitivity, and the control unit is configured to estimate the sensitivity from a slope of the activation plot.

10. The device of claim 7, wherein the one or more key parameters comprises a threshold, and the control unit is configured to estimate the threshold from an intercept of the activation plot.

11. The device of claim 6, wherein the control unit is further configured to:

compare the one or more key parameters with respective ranges; and communicate, based on the comparison, an indication to the patient.

12. The device of claim 6, wherein the control unit is further configured to:

adjust a clinical setting of the implantable device based on the one or more key parameters.

13. The device of claim 12, wherein the one or more key parameters comprises a sensitivity, and the clinical setting is a gain of a feedback controller of the control unit.

14. The device of claim 1, wherein the control unit is configured to monitor the therapy by:

detecting, in each sensed signal, a late neural response evoked by the corresponding second neural stimulus.

15. The device of claim 14, wherein the control unit is configured to estimate a late response threshold from the detected late neural responses.

16. The device of claim 15, wherein the control unit is further configured to:

compare the late response threshold with a range; and communicate, based on the comparison, an indication to the patient.

17. The device of claim 1, wherein the control unit is configured to monitor the therapy by:

measuring, in each sensed signal, an artefact component.

18. The device of claim 17, wherein the control unit is further configured to:

estimate an amount of artefact from the measured artefact components;

compare the amount of artefact with a range; and communicate, based on the comparison, an indication to the patient.

19. The device of claim 17, wherein the control unit is further configured to:

estimate a representative artefact signal from the measured artefact components; and adjust a clinical setting of the implantable device based on the representative artefact signal.

20. The device of claim 1, wherein the control unit is configured to monitor the therapy by:

measuring, in each sensed signal, a latency of a neural response evoked by the corresponding second neural stimulus.

21. The device of claim 20, wherein the control unit is further configured to monitor the therapy by:

estimating a position of the sense electrodes relative to the stimulus electrodes from the measured latencies;

compare the relative position with a range; and communicate, based on the comparison, an indication to the patient.

22. An automated method of monitoring closed-loop neural stimulation therapy, the method comprising:

delivering closed-loop neural stimulation therapy by:

delivering a first neural stimulus to a neural pathway of a patient in order to evoke a neural response on the neural pathway, the stimulus being parametrised by a first stimulus parameter;

measuring an intensity of the neural response evoked by the first neural stimulus, computing, from the measured intensity, a feedback variable;

adjusting, based on the computed feedback variable, the first stimulus parameter; and repeating the delivering, measuring, computing and adjusting to maintain the feedback variable at a target response intensity;

further delivering, interleaved with the first neural stimuli, a plurality of second neural stimuli according to respective second stimulus parameters, wherein the second neural stimuli are different from the first neural stimuli;

receiving a signal sensed subsequent to each delivered second neural stimulus; and monitoring the closed-loop neural stimulation therapy by analysing signals sensed subsequent to respective second neural stimuli of the plurality of second neural stimuli.

23. The method of claim 22, wherein the monitoring comprises measuring, in each sensed signal, an intensity of a neural response evoked by the corresponding second neural stimulus.

24. The method of claim 23, further comprising measure a quality of the evoked neural responses from the measured intensities of the evoked neural responses.

25. The method of claim 24, further comprising:

comparing the measured quality with a threshold; and communicating, based on the comparison, an indicator to the patient.

26. The method of claim 24, further comprising adjusting a clinical setting of the closed-loop neural stimulation therapy based on the measured quality.

27. The method of claim 23, wherein the monitoring further comprises estimating one or more key parameters of the response of the neural pathway to stimuli from the measured intensities of the neural responses.

28. The method of claim 27, wherein estimating the one or more key parameters comprises fitting an activation plot to the measured intensities of the neural responses.

29. The method of claim 28, wherein the activation plot is a Logistic Growth Curve (LGC).

30. The method of claim 28, wherein the one or more key parameters comprises a sensitivity, further comprising estimating the sensitivity from a slope of the activation plot.

31. The method of claim 28, wherein the one or more key parameters comprises a threshold, further comprising estimating the threshold from an intercept of the activation plot.

32. The method of claim 27, further comprising:

comparing the one or more key parameters with respective ranges; and communicating, based on the comparison, an indication to the patient.

33. The method of claim 27, further comprising adjusting a clinical setting of the closed-loop neural stimulation therapy based on the one or more key parameters.

34. The method of claim 33, wherein the one or more key parameters comprises a sensitivity, and the clinical setting is a gain of the adjusting.

35. The method of claim 22, wherein the monitoring comprises detecting, in each sensed signal, a late neural response evoked by the corresponding second neural stimulus.

36. The method of claim 35, further comprising estimating a late response threshold from the detected late neural responses.

37. The method of claim 36, further comprising:

comparing the late response threshold with a range; and communicating, based on the comparison, an indication to the patient.

38. The method of claim 22, wherein the monitoring comprises:

measuring, in each sensed signal, an artefact component.

39. The method of claim 38, further comprising:

estimating an amount of artefact from the measured artefact components;

comparing the amount of artefact with a range; and communicating, based on the comparison, an indication to the patient.

40. The method of claim 38, further comprising:

estimating a representative artefact signal from the measured artefact components; and adjusting a clinical setting of the closed-loop neural stimulation therapy based on the representative artefact signal.

41. The method of claim 22, wherein the monitoring the therapy comprises measuring, in each sensed signal, a latency of a neural response evoked by the corresponding second neural stimulus.

* * * * *